United States Patent
Li et al.

(10) Patent No.: US 8,202,494 B2
(45) Date of Patent: Jun. 19, 2012

(54) APPARATUS AND METHODS FOR LIQUID DROPLET DEPOSITION

(75) Inventors: Liang Li, Edmonton (CA); J. Bryce Young, Edmonton (CA)

(73) Assignee: The Governors of the University of Alberta, Alberta (CA)

( * ) Notice: Subject to any disclaimer, the term of this patent is extended or adjusted under 35 U.S.C. 154(b) by 655 days.

(21) Appl. No.: 11/720,699

(22) PCT Filed: Dec. 2, 2005

(86) PCT No.: PCT/CA2005/001843
§ 371 (c)(1), (2), (4) Date: Aug. 27, 2009

(87) PCT Pub. No.: WO2006/058439
PCT Pub. Date: Jun. 8, 2006

(65) Prior Publication Data
US 2009/0302208 A1  Dec. 10, 2009

Related U.S. Application Data (60) Provisional application No. 60/632,266, filed on Dec. 2, 2004.

(51) Int. Cl.
*G01F 11/00* (2006.01)
*G01N 1/00* (2006.01)
(52) U.S. Cl. .................... 422/521; 422/501
(58) Field of Classification Search .......... None
See application file for complete search history.

(56) References Cited

U.S. PATENT DOCUMENTS

| 5,957,167 | A  | 9/1999 | Feygin |
| 6,116,297 | A  | 9/2000 | Feygin |
| 6,551,557 | B1 | 4/2003 | Rose et al. |
| 2005/0072218 | A1 | 4/2005 | Iwata |

FOREIGN PATENT DOCUMENTS

| CA | 2451314 | 1/2003 |
| GB | 2375315 | 11/2002 |

OTHER PUBLICATIONS

Christer Ericson, et al. "An Automated Noncontact Deposition Interface for Liquid Chromatography Matrix-Assisted Laser Desorption/Ionization Mass Spectrometry", Anal. Chem. 2003, 75, pp. 2309-2315.

*Primary Examiner* — Yelena G Gakh
*Assistant Examiner* — Christopher A Hixson
(74) *Attorney, Agent, or Firm* — Bereskin & Parr LLP/S.E.N.C.R.L., s.r.l.

(57) ABSTRACT

A method of and an apparatus for generating droplets has a capillary tube mounted in a moveable member. The capillary tube is accelerated towards a plate, and then subject to rapid deceleration, e.g. by way of an impact, to promote separation of a droplet which is then deposited on the plate. The droplet can be entirely separated from the capillary tip before being deposited, or, for smaller droplets, the droplet merely extends from the capillary tip and is then drawn onto the plate by a wicking action. The plurality of capillary tubes can be mounted on the common support member to effect multiplexing of drops.

7 Claims, 12 Drawing Sheets

6. Sample results

Figure 7. MALDI spots from post-column addition of matrix to LC-MALDI fractions.

FIG 8

Figure 8. MALDI spectrum of pGlu-fibrinopeptide B from a LC fraction collected on a MALDI plate. 5 fmol of peptide was injected to a capillary C18 column and fractions were collected using the invention.

Figure 10. BSA tryptic digest, 200fmol on column, 60 second fraction at 26 minutes.

| | |
|---|---|
| 1 pmol | MKWVTFISLLLLFSSAYSRGVFRR■■■■■■■■■■■■■GLVLIAFSQYLQQCPFDEHVK■■■■■■■■TCVADESHAGCE<br>K■■■■■■■■■VASLR■■■■■■■■■QEPER■■■■■■■KDDSPDLPKLKPDPNTLCDEFKADEKKFWGK■■■■■■■■■■<br>■■■■■■■YNGVFQECCQAEDKGACLLPKIETMREK■■■■■■QRL■■■■■FGER■■■■■■■■■■■FPKAEFVEVTKLVTDL<br>TKVHK■■■■■■■■■■ADLAKYICDNQDTISSKLK■■■■■■■■■■■■■■■■■■■■■■■■■■■■■■■DVCK■■■■■■<br>■■■■■■■■■■■■■■LAK■■■■■■■■■■■■■■■■■■■■■■■■■■■■■■■■■■■■■■■■■■■■■■■■■YT<br>R■■■■■■■■■■■SLGKVGTR■■■■■■■■■MPCTEDYLSLILNRL■■■■■■■■■■■■CCTESLVNR■■■■■■■■■■<br>■AFDEKLFTFHADICTLPDTEKQIK■■■■■■■■HKPK■■■■■■■■■■■■■■■■■■■■■■■■■■LVVSTQTALA |
| 200 fmol, 60 s fraction | MKWVTFISLLLLFSSAYSRGVFRRDTHKSEIAHR■■■■■■■GLVLIAFSQYLQQCPFDEHVK■■■■■■■■TCVADESHAGCE<br>K■■■■■■■■■VASLRETYGDMADCCEKQEPER■■■■■■DDSPDLPK■■■■■■■■■■■■ADEKKFWGK■■■■■■RHPYFYA<br>PELLYYANKYNGVFQECCQAEDKGACLLPKIETMREKVLASSARQRLRCASIQKFGERALKAWSVARLSQKFPK■■■■■■LVTDL<br>TKVHKECCHGDLLECADDRADLAK■■■■■■■■■■■■■■■■■■■■■■■■■■■■■■■■■■■DVCKNYQEAKDA<br>FLGSFLYEYSR■■■■■■■■■LAK■■■■■■■■■■■■■LK■■■■■■■■■■■■■■■■■■■■■■■■■■■■YT<br>RKVPQVSTPTLVEVSRSLGKVGTRCCTKPESERMPCTEDYLSLILNRLCVLHEKTPVSEKVTK■■■■■■■■RPCFSALTPDETYVP<br>KAFDEKLFTFHADICTLPDTEKQIK■■■■■■■HKPKATEEQLK■■■■■■■■■CCAADDK■■■■■■■LVVSTQTALA |
| 200 fmol 30 s fraction | MKWVTFISLLLLFSSAYSRGVFRR■■■■■■■■■■■■■GLVLIAFSQYLQQCPFDEHVK■■■■■■■■■■■■■<br>■SLHTLFGDELCKVASLR■■■■■■■QEPER■■■■■■DDSPDLPK■■■■■■■■■■■■ADEKKFWGK■■■■■■RHPYFYA<br>PELLYYANKYNGVFQECCQAEDKGACLLPKIETMR■■■■■■QRLRCASIQKFGERALKAWSVARLSQKFPK■■■■■■LVTDL<br>TKVHKECCHGDLLECADDRADLAK■■■■■■■■■■■■■■■■■■■■■■■■■■DAIPENLPPLTADFAEDKDVCKNYQEAKDA<br>FLGSFLYEYSRRHPEYAVSVLLRLAK■■■■■■■■■■■■■■LK■■■■■■■■■■■■■■■LGEYGFQNALIVRYT<br>RKVPQVSTPTLVEVSRSLGKVGTRCCTKPESERMPCTEDYLSLILNRLCVLHEK■■■■■■■■RPCFSALTPDETYVP<br>KAFDEKLFTFHADICTLPDTEKQIK■■■■■■■HKPKATEEQLKTVMENFVAFVDKCCAADDK■■■■■■■LVVSTQTALA |
| 10 fmol | MKWVTFISLLLLFSSAYSRGVFRRDTHKSEIAHR■■■■■■■GLVLIAFSQYLQQCPFDEHVKLVNELTEFAKTCVADESHAGCE<br>K■■■■■■■■■VASLRETYGDMADCCEKQEPERNECFLSHKDDSPDLPKLKPDPNTLCDEFKADEKKFWGK■■■■■■RHPYFYA<br>PELLYYANKYNGVFQECCQAEDKGACLLPKIETMREKVLASSARQRLRCASIQKFGERALKAWSVARLSQKFPKAEFVEVTKLVTDL<br>TKVHKECCHGDLLECADDRADLAKYICDNQDTISSKLKECCDKPLLEKSHCIAEVEKDAIPENLPPLTADFAEDKDVCKNYQEAKDA<br>FLGSFLYEYSRRHPEYAVSVLLRLAK■■■■■■■■■■DDPHACYSTVFDKLKHLVDEPQNLIKQNCDQFEKLGEYGFQNALIVRYT<br>R■■■■■■■■■SLGKVGTRCCTKPESERMPCTEDYLSLILNRLCVLHEKTPVSEKVTKCCTESLVNRRPCFSALTPDETYVP<br>KAFDEKLFTFHADICTLPDTEKQIKKQTALVELLKHKPKATEEQLKTVMENFVAFVDKCCAADDKEACFAVEGPKLVVSTQTALA |
| 5 fmol | MKWVTFISLLLLFSSAYSRGVFRRDTHKSEIAHRFKDLGEEHFKGLVLIAFSQYLQQCPFDEHVKLVNELTEFAKTCVADESHAGCE<br>KSLHTLFGDELCKVASLRETYGDMADCCEKQEPERNECFLSHKDDSPDLPKLKPDPNTLCDEFKADEKKFWGKYLYEIARRHPYFYA<br>PELLYYANKYNGVFQECCQAEDKGACLLPKIETMREKVLASSARQRLRCASIQKFGERALKAWSVARLSQKFPKAEFVEVTKLVTDL<br>TKVHKECCHGDLLECADDRADLAKYICDNQDTISSKLKECCDKPLLEKSHCIAEVEKDAIPENLPPLTADFAEDKDVCKNYQEAKDA<br>FLGSFLYEYSR■■■■■■■■■LAKEYEATLEECCAKDDPHACYSTVFDKLKHLVDEPQNLIKQNCDQFEK■■■■■■■■YT<br>R■■■■■■■■SLGKVGTRCCTKPESERMPCTEDYLSLILNRLCVLHEKTPVSEKVTKCCTESLVNRRPCFSALTPDETYVP<br>KAFDEKLFTFHADICTLPDTEKQIKKQTALVELLKHKPKATEEQLKTVMENFVAFVDKCCAADDKEACFAVEGPKLVVSTQTALA |

APPARATUS AND METHODS FOR LIQUID DROPLET DEPOSITION

This application claims the benefit of U.S. Provisional Application No. 60/632,266 filed Dec. 2, 2004, and the entire contents of which are hereby incorporated by reference.

The section headings used herein are for organizational purposes only and are not to be construed as limiting the subject matter described in any way.

FIELD

This invention relates to mass spectroscopy, and more particularly this invention relates to the preparation of samples for use in matrix assisted laser desorption ionization (MALDI) mass spectroscopy.

INTRODUCTION

Electrospray ionization (ESI) and matrix assisted laser desorption ionization (MALDI) are complementary ionization techniques for generating ions for mass spectrometry (MS) in the field of proteomics. Liquid chromatography (LC) is typically interfaced to ESI-MS instruments to give online sample separation and MS analysis. However, MALDI demonstrates marked robustness towards contaminants, and features greater analysis speed and reduced sample consumption. MALDI, however, is not amenable to a direct interface with LC, and thus the sample separation power of chromatography is not easily available to MALDI-MS.

LC-MALDI refers to techniques that attempt to bridge the gap between LC and MALDI. There are a number of known proposals for an off-line LC-MALDI interface. In addition, the invention can be useful to other areas of applications such as in tissue imaging by MALDI. Tissue imaging by MALDI involves producing thin slices of tissue, and directly or indirectly using MALDI-MS to create a mass spectral map of the tissue, based on the chemical/protein environment. Where this invention is applicable is in the deposition of a MALDI matrix at discrete locations on the tissue slice.

One known proposal is the Probot LC-MALDI interface by LC Packings (CA, USA), which is based on a blotting technique, where the liquid fractions from an LC are deposited by touching the capillary tip to the receiving plate. However, this blotting technology has certain limitations. To successfully blot a droplet, the droplet must grow to a certain size (hundreds of nanoliters), limiting the technology to relatively high flow experiments and for chromatographic separations that produce broad peaks. For fast chromatography such as monolithic column separation, the droplet dropping rate afforded by the blotting technique is too slow. Another limitation of the blotting technique is that the tip makes contact with the plate, making the receiving surface vulnerable to damage. Thus it cannot be used for applications that require the deposition surface to remain undisturbed, such as in MALDI tissue imaging where matrix is deposited onto a tissue sample placed on a MALDI plate.

Another recent concept reported in Anal. Chem. (2003, 75, 2309-2315) is to apply a high voltage between the capillary tip and the MALDI plate and use the electric force to drive the droplet down from the tip to the plate. The upper limit of the dropping speed of this method is unknown. The technique requires the use of a conductive receiving plate, precluding it from more general use, such as sample or matrix deposition to a non-conductor such as a glass slide. It involves high voltage (2000-4000 V) which can make the device more expensive to construct, and introduces special precautions which must be taken during operation.

SUMMARY

In accordance with a first embodiment of the invention, there is provided an apparatus for generating a fraction from a liquid sample, the apparatus comprising:
 (a) a capillary tube including a capillary tip;
 (b) a moveable element with the capillary tube mounted to the moveable element;
 (c) an actuating means for displacing the moveable element and connected thereto; and
 (d) a stop member, located to limit the travel of the moveable element, whereby, in use, actuation of the actuation means displaces a moveable element until the moveable element abuts the stop member, to rapidly decelerate the moveable element and the capillary tube, to promote the separation of a droplet from the tip of the capillary tube.

The capillary tube can be mounted within a support tube.

Moreover, any suitable actuation means can be used, but it preferably comprises a solenoid and a solenoid core mounted on the support tube. The locations of the solenoid and the core can be reversed.

The actuation means can include a spring means, acting on the moveable element, to displace the moveable element to a normal position.

The stop member can be mounted on the support tube and can be generally cylindrical, but it is to be understood that it is not limited to such a configuration. Moreover, a fixed abutment member can be located adjacent the stop member and can include an aperture for passage of the support tube and the capillary tube.

Further, the apparatus can include means for supporting a support plate for receiving droplets adjacent the capillary tip.

In addition, the apparatus can include a means for locating the support plate at a first position sufficiently spaced from the capillary tip to promote complete separation of larger droplets from the capillary tip before the droplets contact the plate, and a second position in which the plate is located closer to the capillary tube, for enabling smaller droplets to be drawn onto the plate by wicking action for complete separation of the droplets from the capillary tip.

Moreover, the apparatus can include a support member and a plurality of capillary tubes, each including a respective capillary tip mounted in the support member, the tips of the capillary tubes being mounted in a generally common plane, for enabling simultaneously deposition of a plurality of fractions onto a plate.

The capillary tip can be coated with a hydrophobic coating.

Another aspect of the present invention provides a method of generating a fraction from a liquid sample for analysis, the method comprising:
 (1) supplying the sample to a capillary tube;
 (2) locating the tip of the capillary tube adjacent a plate;
 (3) accelerating the capillary tube towards the plate; and
 (4) subjecting the capillary tube to rapid deceleration to promote separation of a droplet from the tip of the capillary tube whereby momentum of the droplet causes the droplet to at least extend towards the plate to promote transfer of the droplet to the plate.

Rapid deceleration of the capillary tube can be effected by means of impact against an abutment member.

Further, the method comprises, to form large droplets, mounting the capillary tube sufficiently spaced from the plate, to cause droplets to be entirely separated from the capillary tube before contacting the plate.

In another aspect, the method comprises, to form small droplets, mounting the capillary tip sufficiently close to the plate whereby a droplet at the capillary tip extends and elongates and contacts the plate before complete separation from the capillary tip, whereby deposition of the droplet on the plate is promoted by a wicking action.

Moreover, the method can include adding matrix material to the liquid solution, prior to supply to the capillary tube.

The method can also include mounting a plurality of capillary tubes on a common support member, supplying each of the capillary tubes with a liquid sample, and simultaneously subjecting the support member and all the capillary tubes to rapid deceleration, to deposit a plurality of droplets as fractions, simultaneously, onto the plate.

Moreover, the method can include providing a tissue sample on the plate and providing at least one droplet on the tissue sample.

BRIEF DESCRIPTION OF THE DRAWINGS

The skilled person in the art will understand that the drawings, described below, are for illustration purposes only. The drawings are not intended to limit the scope of the applicants teachings in any way.

FIG. 14 is a sequence coverage of BSA by LC-MALDI MS/MS of the digests using different amounts of sample loading;

DESCRIPTION OF VARIOUS EMBODIMENTS

Figure 1:
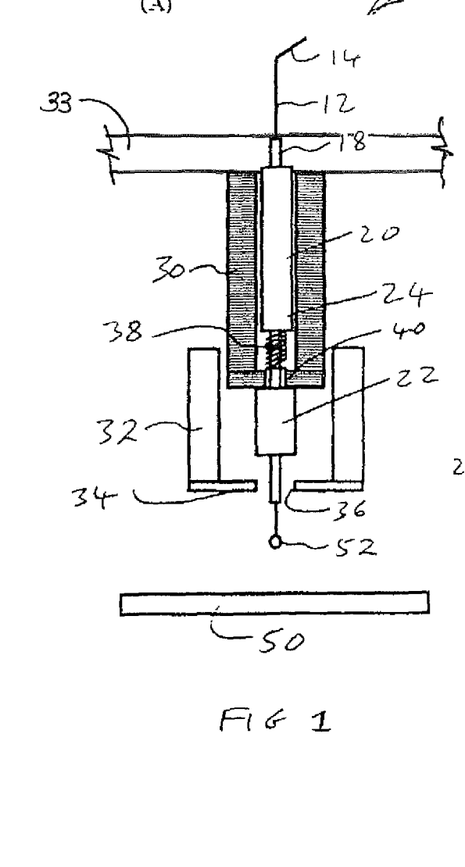
FIG. 1 shows, schematically, an apparatus in accordance with a first embodiment of the present invention.

Referring first to FIG. 1, the apparatus of the present invention is indicated generally by the reference 10, having a capillary tube 12, that has an inlet end 14, for connection to a liquid supply and an outlet end or tip 16, providing a tip for formation of droplets.

The capillary tube 12 is mounted in a support tube 18, here a metal tube, to provide the necessary constructional integrity to the capillary tube 12. The metal tube 12 is itself mounted in a solenoid core 20. A stop member 22 is mounted on a lower end of the metal tube 18.

A solenoid for actuating the apparatus is indicated at 30 and is mounted with respect to a support 32. A plate 34 is mounted across the bottom of the support 32 and includes an aperture 36, through which the capillary and metal tube can extend. The aperture 36 is sized so that the stop member 22, when traveling downwards, abuts the plate 36 and is stopped.

It will be understood that the plate 34 does not necessarily have to be in the form of a plate and it is sufficient if there are one or more projections to engage and stop the stop member 22.

The capillary tube 12, metal tube 18, solenoid core 20 and stop member 22 comprise a moveable element 24 that, as will be detailed, can be displaced downwards by the action of the solenoid 30. To keep this moveable element 24 displaced in a normal or upper position, a coil spring 38 is provided around the metal tube 18, below the solenoid core 20, and abutting an inwardly projecting lip 40 at the bottom of the solenoid 30. Like the aperture 36 and the plate 34, the inwardly projecting lip 40 can be in the form of an aperture or a hole in a plate, or it can be in the form of one or more projections sufficient to support the bottom end of the spring 38. Accordingly, FIG. 1 shows the normal position of the device, when the solenoid 30 is not activated.

In use, to generate a droplet, power is supplied to the solenoid 30 to actuate it. A small DC voltage is applied over a very short time period (typically 0.10 sec) to actuate the solenoid. The shape of the voltage pulse is a square wave, although other wave shapes are possible. This generates a downward force on the moveable element 24 accelerating it downwards towards the plate 34. The element 24 accelerates to a maximum velocity, until the metal stop member 22 contacts the plate 34. This contact creates an impact rapidly decelerating the moveable element 24 to a stopped position.

In use, the apparatus 10 is mounted above a plate 50 for receiving one or more sample droplets, and the apparatus 10, preferably, is integral with a table for supporting the plate 50 at a desired height relative to the outlet and or tip 16 of the capillary 12. As is explained further below, the spacing between the tip of the capillary 12 and the plate 50 can be varied, depending upon the size of the sample droplets.

Further in use, liquid sample is supplied to the inlet end 14 of the capillary 12. As the liquid sample is supplied, a droplet will start to form at the capillary tip 16, as indicated at 52.

A sudden impact of the stop member 22 against the plate 34 generates an impact force that dislodges the droplet 52 from the capillary tip 16. The tip may be coated with a hydrophobic coating to reduce droplet adhesion to the capillary.

Figure 2:
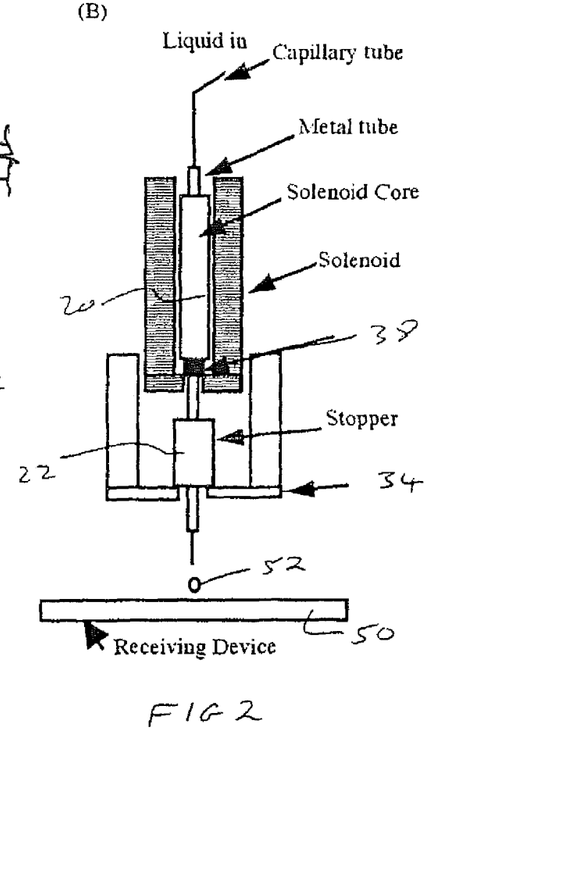
FIG. 2 shows use of the apparatus of FIG. 1 to generate a relatively large drop.

FIG. 1 shows the basic configuration of a first embodiment of the apparatus adapted for generating relatively large droplets, greater than 100 nl, and for this purpose the capillary tip 16 is located a relatively large distance above the plate 50. FIG. 2 shows operation of this first embodiment of the apparatus.

In use, when the moveable element 24 is displaced downwards and impacts the plate 34, the droplet 52 is displaced from the outlet end or tip 16, and due to its momentum, travels downwards and comes to rest on the plate 50. Note that the spacing from the plate is sufficient to ensure that the droplet completely separates from the capillary tip 16, before it contacts the plate 50.

FIGS. 3a-3d show a second embodiment of the apparatus, that corresponds generally with the first embodiment of FIGS. 1 and 2, so that like components are given the same reference numeral. A shown in FIG. 3a, the principal difference is that the tip 16 of the capillary is now closer to the plate 50, to enable smaller droplets, less than 100 nl, to be formed and to be transferred by a modified technique as detailed below.

Figure 3A:
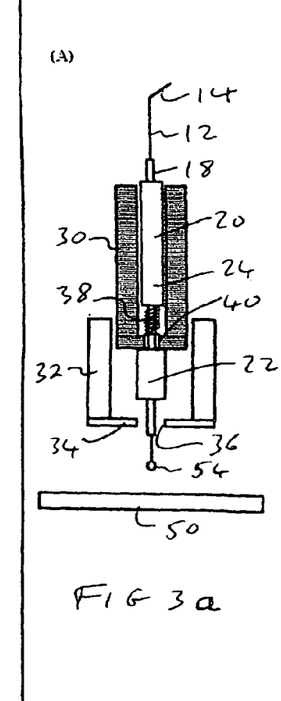
FIGS. 3*a*-3*d* show an apparatus in accordance with a second embodiment of the present invention, and a sequence for generating or transferring and transferring a smaller droplet.
Figure 3B:
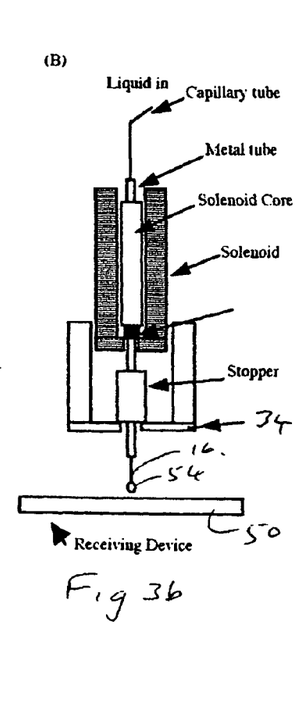
Figure 3C:
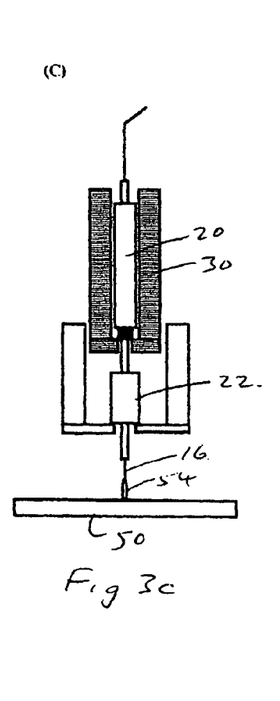
Figure 3D:
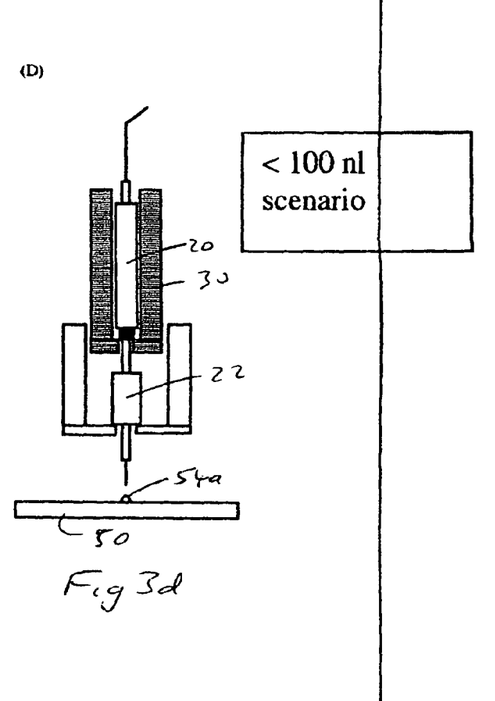

FIG. 3b shows a droplet 54 just as the impact commences, before the severe decelerating affects of the impact have distorted the droplet, and it will be understood that, in all these figures, the droplet is, to a large extent, shown schematically. In FIG. 3c, the droplet 54 is shown elongating and extending downwards from the capillary tip 16 due to the decelerating effect of the impact, until it contacts the plate 50. This enables the droplet to transfer by a wicking action and does not require the droplet to separate from the tip 16 and transfer by momentum to the plate 50. Finally in FIG. 3d, the droplet 54 is shown detached from the capillary tip 16, so as to be deposited on the plate 50, as indicated at 54a.

Power to the solenoid 3 is then turned off, and the spring 38 will return the moveable element 24 to its normal or rest position shown in FIG. 3a. The apparatus 10 is then ready for generation of the next droplet. For this purpose, the plate 50 would be indexed to present a fresh position for the next droplet, the size of the next droplet, will depend upon the waiting period selected between droplets and the flow rate of the liquid.

For the technique described in relation to FIGS. 3a-3b, unlike the FIG. 2 embodiment, the capillary tip or outlet end 16 is positioned close enough to the plate 50 to enable the elongated droplet 52 to contact the plate 50, before separation. This is necessary, since the droplet that is less than 100 nl cannot be separated, or reliably separated, from the capillary 12 by this technique.

For both embodiments, the separation of the capillary tip in both positions (top and bottom) is somewhat arbitrary, but is related to the type of fluid (and the size of the fluid droplet) being deposited. At the top position, the separation between capillary tip and plate surface is, usually, several millimeters. At the bottom position, the separation is, usually, several hundred microns (micrometers) to a millimeter.

With respect to actual velocity and acceleration figures. The inventor has calculated some values, although the actual values are expected to be approximately 20% higher. The calculated values are:

average velocity=0.09 m/s average acceleration=5.4 m/s$^2$ average force applied=0.09N These values assume that the deceleration on impact to be instantaneous, since the impact is against bulk aluminum, which is known to be rigid.

Figure 4:
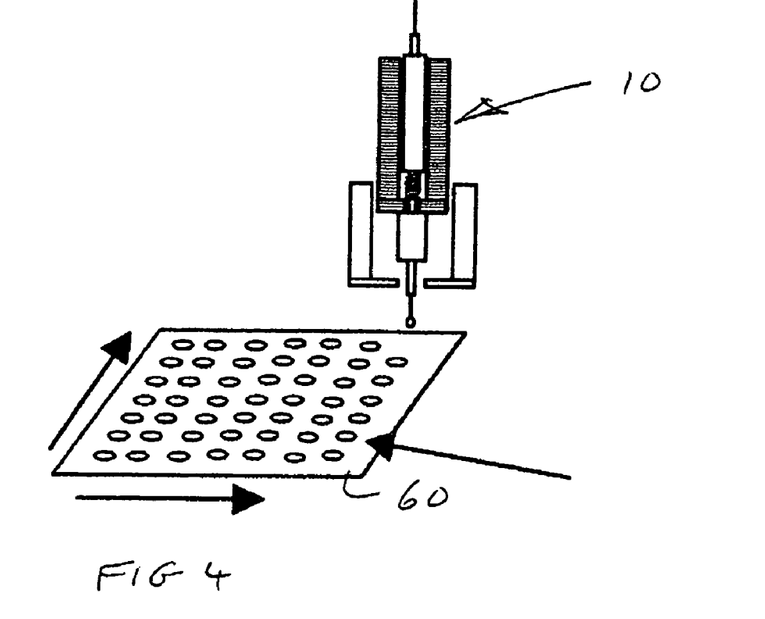
FIG. 4 is a perspective view showing use of the apparatus of the present invention to provide a two-dimensional array of droplets on a MALDI plate.

Turning now to FIG. 4, this shows the apparatus 10 used in conjunction with a plate 60 enabling a two-dimensional array of sample spots to be deposited on it. The plate 60 is mounted on a two-dimensional translational stage. The two-dimensional stage is driven, and moves the plate 60 in the manner of raster, in the two dimensions, to generate a two-dimensional array of spots. Thus, the plate 60 is moved in a predefined path to predefined positions to collect fractions from the deposition apparatus 10.

The collection fractions, once dried, can be loaded directed into a MALDI-MS for analysis.

Figure 5:
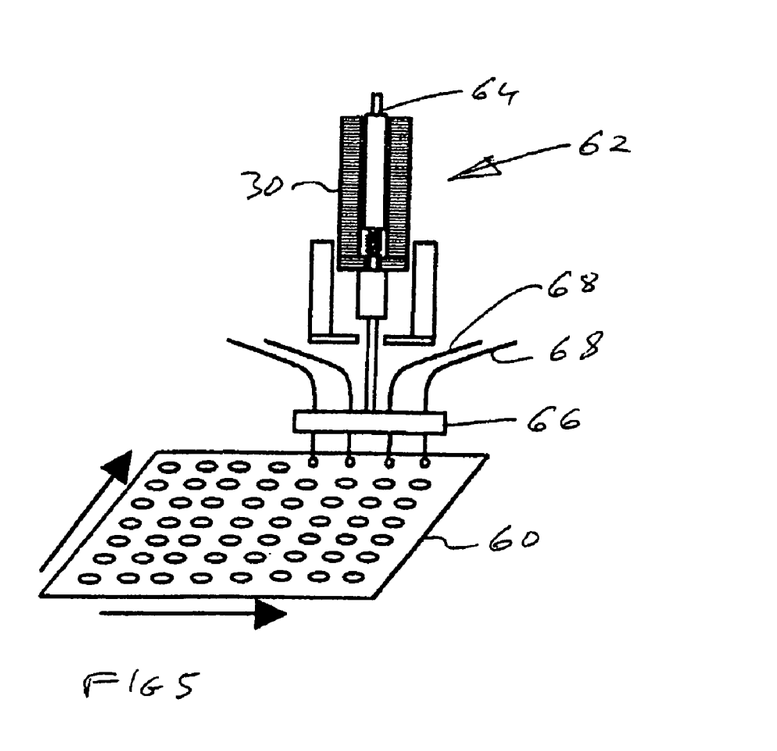
FIG. 5 shows a variant of the apparatus of FIG. 4, including the ability to multiplex different samples and generate the two-dimensional array on the MALDI plate.

FIG. 5 shows a variant of the arrangement shown in FIG. 4, adapted for multiplexing, for parallel depositions. Here, the capillary 12 through the center of the solenoid is omitted. Instead, the tube 18 is replaced with a rod 64 that extends down through the solenoid 30. Attached to the bottom of the rod 64 is a cross member 66. It will be understood that this arrangement is shown purely schematically, and the mechanical details will be such as to ensure that each of the capillaries, detailed below, is subject to the same impact and sudden deceleration effect.

Here, a plurality of capillaries 68, four being shown in the drawing, are connected through the cross member 66. With four capillaries, for each actuation of the apparatus 62, four spots are deposited on the plates 60 in a predetermined spacing.

Again, the collected fractions after drying can be inserted into a MALDI-MS for analysis.

Another technique commonly used is analysis of tissue. The use of this invention for this application shown in FIG. 6. To analyze tissue, a plate 70 has a thin slice of tissue sample indicated schematically 72 placed upon it.

It is commonly desirable to analyze different selected points on the tissue sample, and it is usually desired to have these in a non-standard array.

For this purpose, current techniques are often performed manually, with the matrix spots being deposited by a hand-operated pipet. The matrix spots each promote the generation of ions from the tissue sample at that particular spot.

The limitations of this known method are the slow speed of manual spot deposition, combined with the difficulty of producing a regular and systematic pattern of matrix spot on the tissue section of interest.

Figure 6:
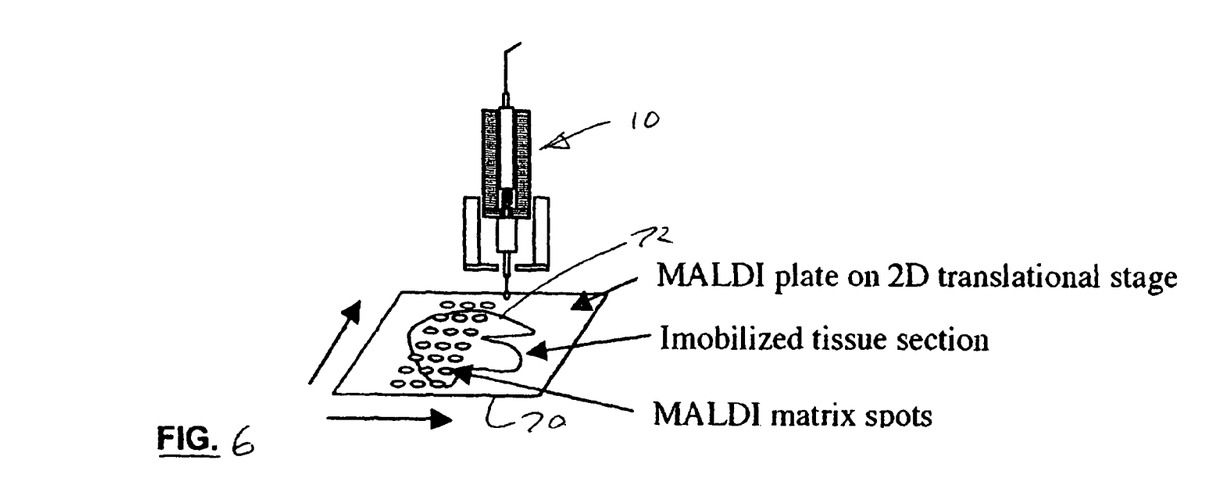
FIG. 6 shows use of the apparatus of the present invention to provide a two-dimensional array of droplets on a tissue sample, in accordance with the present invention.

With the present invention, shown in FIG. 6, the apparatus 10, or even the multiplexing apparatus 62 of FIG. 5, can be used to deposit hundreds of thousands of spots on the tissue sample in a relatively short period of time. The use of a two-dimensional translational stage engages these spots to be located accurately on the desired grid pattern. The apparatus 10 enables enable fine control over both spot size and spot placement, affording significant gains over known manual techniques.

Figure 7:
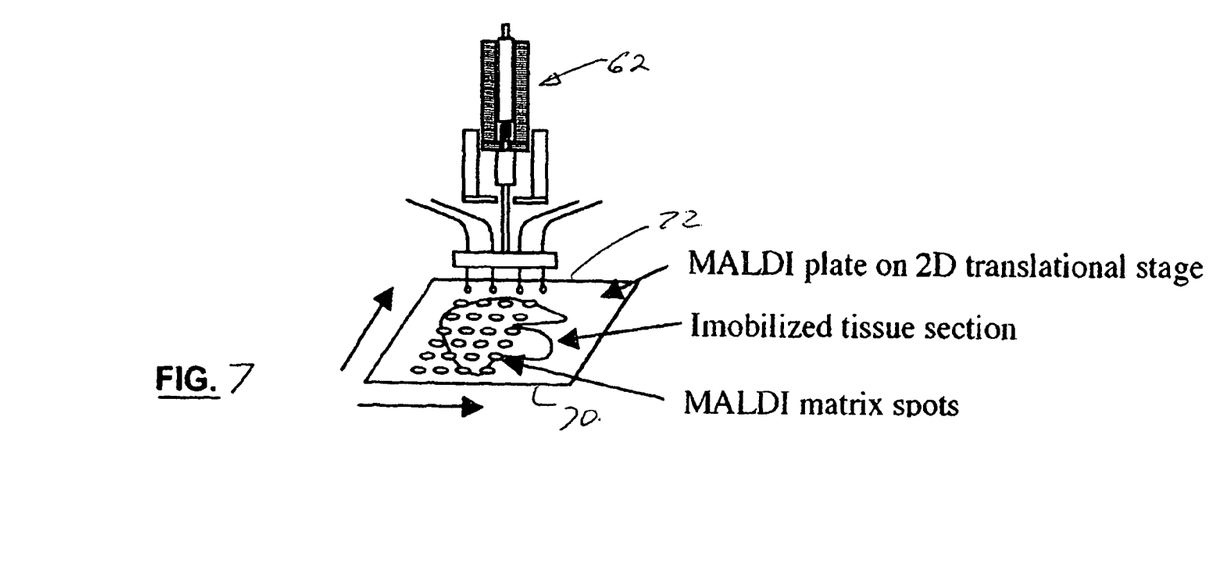
FIG. 7 shows a variant of the apparatus of FIG. 6, including multiplexing a number of samples and generating a two-dimensional array on a tissue sample.

FIG. 7 shows the use of the multiplexing apparatus 62 of FIG. 5 employed with a tissue sample.

The present invention can also be used in the analysis of small molecules such as organic pharmaceuticals. In this application, the device can be used to deposit sample on the mounting plate, and again, for parallel applications, the apparatus of FIG. 5 can be used to multiplex the samples and deposit multiple spots simultaneously.

Figure 8:
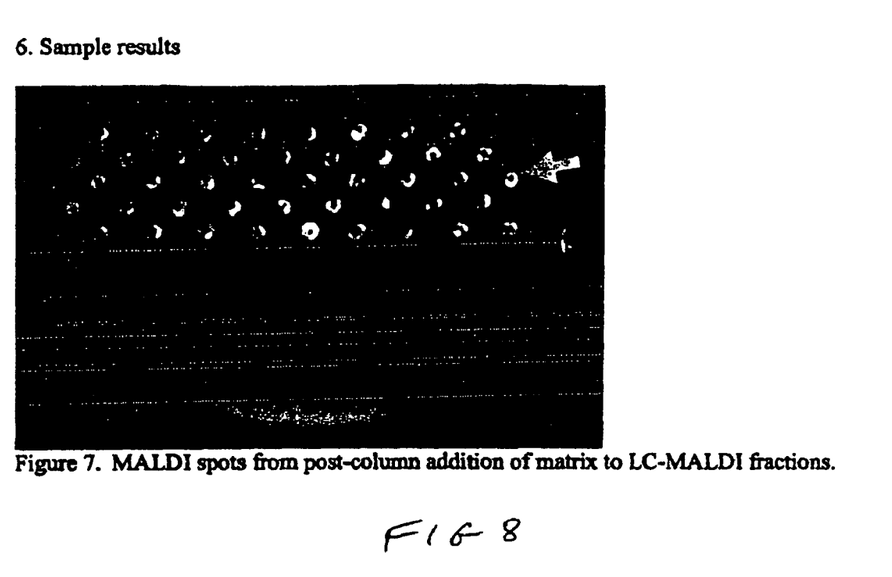
FIG. 8 shows a formation of MALDI spots on a plate from post-column addition of matrix to LC-MALDI fractions.

Referring to FIG. 8, this shows of the appearance of MALDI spots on a sample plate, after the fractions have been deposited on the plate. Here, fractions are taken from a liquid chromatograph (LC), and matrix is added to the liquid as it elutes from the column.

Figures 8, 9:
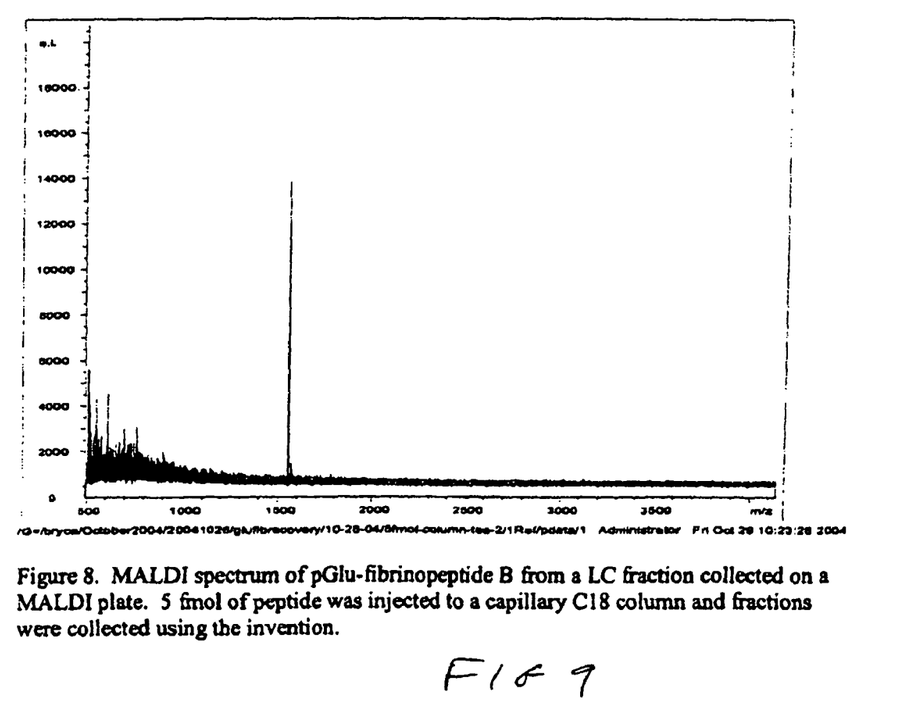
FIGS. 9-11 show spectra generated from MALDI samples formed in accordance with the present invention.
Figure 10:
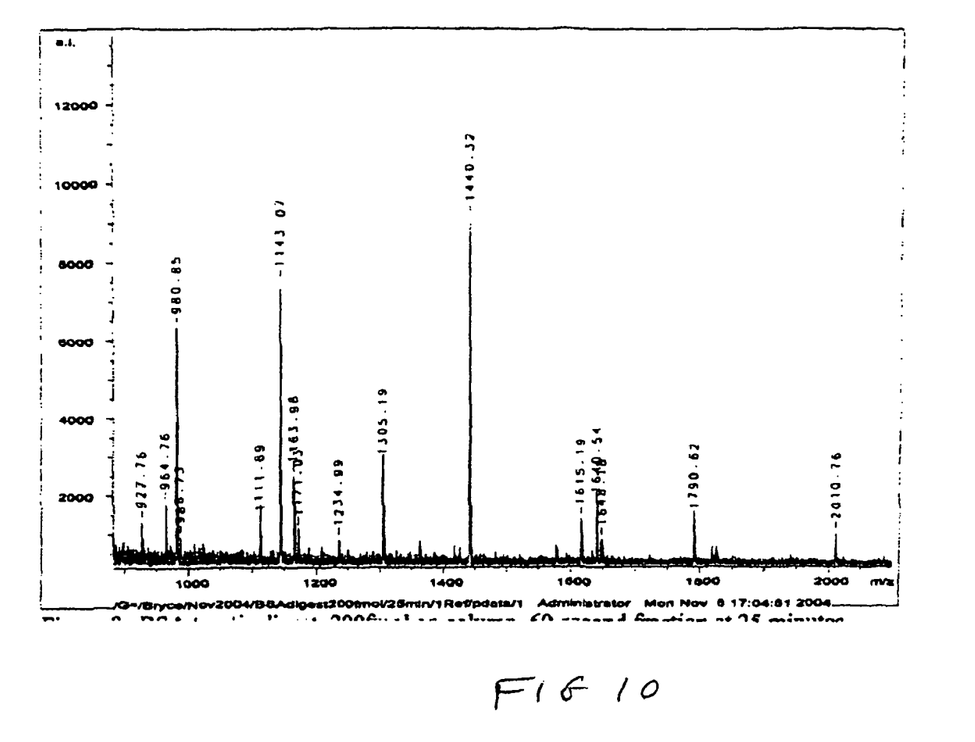
Figures 10, 11:
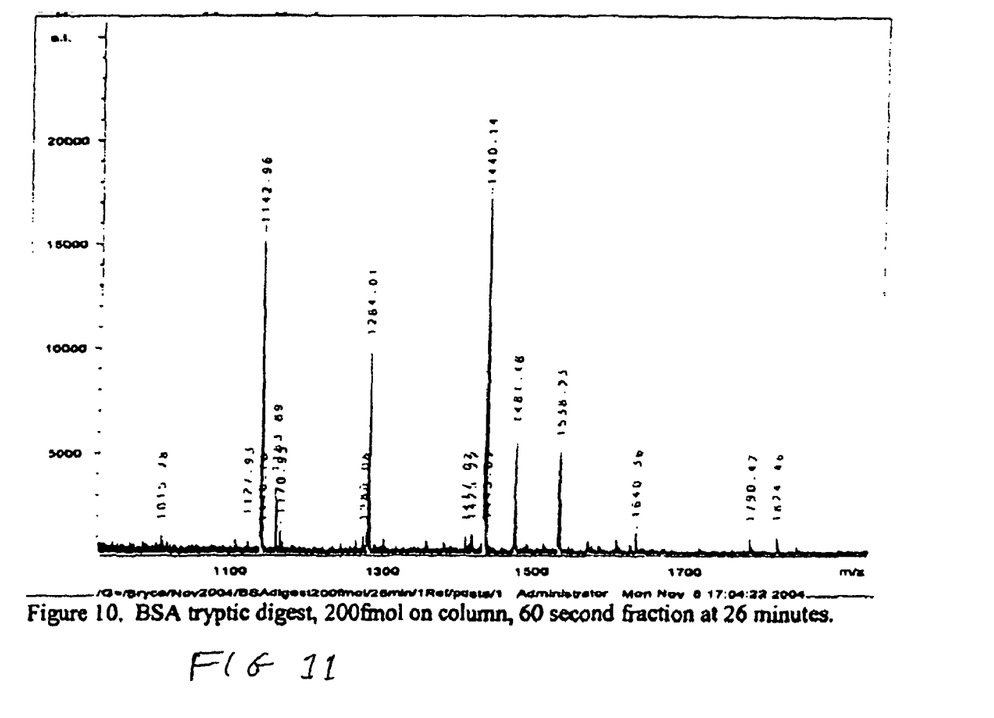

FIGS. 9, 10 and 11 show MALDI spectra obtained using the present invention. These demonstrate that the device functions as intended. Since the device serves to fractionate a flowing liquid stream, into many small fractions, it can give improved resolution. The flowing liquid stream can contain many discrete components that elute from the exit of the capillary at different times. Collecting shorter fractions affords better resolution, allowing one to focus on fewer components in any given fraction. Collecting longer fractions may maximize the amount of one particular component in a given fraction. This maximizes the probability of detection using a mass spectrometer.

FIG. 9 shows how a very long fraction can be used to detect a component that is present only in very small amounts.

FIGS. 10 and 11 are actually a series of two fractions, intended to demonstrate the chromatographic resolution of a very complex mixture. Some of the peaks in each mass spectrum are common, indicating that some components are eluting during the collection of both fractions. However, most peaks are dissimilar, indicating that the fractionation is successful at spatially resolving different components on different spots. (As a side note, these figures also demonstrate that the plumbing system used to interface the solenoid spotter to the liquid chromatograph does not introduce a phenomenon known as "dead-volume" into the system, which reduces the resolution.)

It will be appreciated that while specific embodiments of the invention have been shown and described, numerous variations are possible within the scope of the present invention. For example, while a solenoid has been shown as an actuating device for displacing the capillary, it will be understood that any suitable actuator can be used. The actuator could be driven hydraulically, pneumatically, or by other mechanical means. All that is essential is that the actuator be capable of accelerating the capillary and the capillary tip to a velocity such that, upon impact with the stop member, the rapid deceleration on impact promotes the separation of a droplet. In the case of larger droplets, the droplet may be entirely separated from the tip of the capillary, before contacting the plate on which it is to be deposited; for smaller droplets, the configuration can be such as to promote elongation of the droplet, so that it contacts a surface and a wicking action then causes the droplet to be absorbed onto the surface.

Also, even when a solenoid is used as the actuator, the positions of the solenoid core and coil could be reversed. Thus, the solenoid could be mounted to move with the capillary tube and the core could be stationary, and likely then would need to be of different mechanical configuration. This arrangement, while possible, would require that power be supplied to a moving coil and hence it is not so convenient.

Further, while the invention has been shown and described as having the capillary tube accelerate vertically downwards, this might not be essential, and for some uses, it is possible that the plate could be mounted in an other than a horizontal position, with the rest of the apparatus configured accordingly. Mounting the plate horizontally does have the advantage that droplets, before drying, will have not tendency to move or migrate across the plate.

EXAMPLES

Aspects of the applicant's teachings may be further understood in light of the following examples, which should not be construed as limiting the scope of the present teachings in any way.

Example 1

Experimental Section

Materials and Reagents. HPLC grade acetonitrile (ACN) and methanol (MeOH) were obtained from Fisher Chemicals (Fairlawn, N.J.), and filtered prior to use. Water ($H_2O$) was deionized with a Millipore deionizer to 18 MOhm and filtered through a 22 μm filter prior to use. Dithiothreitol (DTT), iodoacetamide (IAA), trifluoroacetic acid (TFA), bovine serum albumin (BSA), trypsin enzyme, and pyro-Glu-fibrinopeptide (pyroGFP) were obtained from Sigma Aldrich (St. Louis, Mo.) at the highest available purity. 2,5-dihydroxybenzoic acid (DHB) was obtained from Sigma Aldrich at 98% purity, and recrystallized prior to use three times in ethanol, and once in water. DHB was dissolved in methanol to a final concentration of 100 mg/mL before use.

E. coli Protein Extraction. E. coli extracts were prepared by a solvent suspension method. Lyophilized E. coli cells (6 mg) were suspended in 2 mL of 10 mM Tris-HCl buffer (pH 7.90) in a centrifuge tube and sonicated for 1 min with a probe tip sonicator (Branson Sonifier 450, Branson Ultrasonics, Danbury, Conn.) while the centrifuge tube was immersed in an ice bath. The suspension was centrifuged at 11750 g for 10 min. The supernatant was transferred in 500 μL aliquots to Microcon-3 3000 Da molecular weight cutoff filters (Millipore, Billerica, Mass.) and centrifuged at 13000 g for 30 min. The filtrate was collected, pooled, and the protein content quantified by Bradford assay, using γ-globulin as a protein standard.

Enzymatic digestion. 5 μL of protein in solution was added to 5 μL of 0.1 M $NH_4HCO_3$ buffer. One μL of 45 mM DTT was added to the solution, and the solution was incubated for 20 min at 37° C. One μL of 100 mM iodoacetamide was added, and the solution was stored in the dark for 15 min at room temperature. 0.5 μL of 1 μg/μL trypsin solution was added to this mixture, and incubated for 18 hours at 37° C. The digestion was stopped with the addition of 0.1% TFA.

Chromatographic System. An Agilent 1100 Capillary HPLC system (Palo Alto, Calif.) was used to perform the reversed phase separation on a 150 μm×15 cm C18 column (Grace Vydac, Hesperia, Calif.). A reproducible flow rate of 1 μL/min through the column was achieved by using a chromatographic splitter, installed upstream of the sample injector. The pump was operated at a flow rate of 100 μL/min, and the split ratio was adjusted to approximately 100:1. The flow rate was subsequently tested using volumetric glass capillaries. The mobile phase gradient was generated using a binary mixture of A: 0.1% TFA in 4% ACN/$H_2O$, and B: 0.1% TFA in ACN. The gradient program used was 0% B for 5 minutes, 0-15% B from 5 to 7.5 min, 15-25% B from 7.5 to 25 min, 25-35% B from 25 to 35 min, and 35-80% B from 35 to 55 min.

Impulse-driven Deposition Device. A diagram of the deposition system is shown in FIG. 1A. The micro-depositor consists of a small solenoid coil (TP6X12-I-24D, Guardian Electric, Woodstock, Ill.) which is mounted in place with a homebuilt cradle/motion control system. The solenoid core is a homebuilt hollow ferromagnetic steel dowel, with a custom fitted steel capillary. A fused silica capillary (i.d. 50 μm and o.d. 180 μm) is threaded through the inner diameter of the steel capillary (i.d. 200 μm and o.d. 1/16 in.) and is fixed in place at the top of the solenoid core assembly with standard fittings and a union (VICI/Valco, Houston, Tex.).

The solenoid assembly is mounted on a x,y,z micro-adjustment stage (1.75" three axis centre drive positioning stage, Edmund Optics, Barrington, N.J.). The assembly is positioned above motorized translation tables, as shown in FIG. 1B (MX80S, Parker Hannifin, Rohnert Park, Calif.). The motor drivers, computer control card, breakout board and cables required for the motion tables were acquired from the manufacturer. The solenoid is operated by a homebuilt power supply with an internal function generator which produces a square wave. The power supply can be remotely toggled via a gated logic signal, which is triggered through the break-out board. The motion tables and solenoid power supply are controlled by a program that was written using the supplied software development tools (ACR-View, Parker Hannifin Compumotor Division, Rohnert Park, Calif.).

Matrix Addition. Matrix was added during the deposition via a post-column T-connection (VICI/Valco, Houston, Tex.). DHB solution was infused into the T-connection using a syringe pump (Cole-Parmer, Vernon Hills, Ill.) at a flow rate of 1 μL/min. The LC fractions were deposited on a 100-spot MALDI target (Applied Biosystems, Foster City, Calif.) that was fixed into position on the motion tables by a homebuilt mounting adapter.

Mass Spectrometry. MALDI MS data were acquired either using a MALDI time-of-flight (TOF) mass spectrometer (Bruker Reflex, Bremen, Germany) in a reflectron mode, or using the Sciex Qstar Pulsar-i Quadrupole-TOF (QqTOF) mass spectrometer (Applied Biosystems, Concord, ON). MS/MS spectra were collected using the Qstar instrument. The Information Dependent Acquisition (IDA) system was used to automatically and independently acquire MS/MS data. The orthogonal MALDI source came equipped with sampling algorithms that were used to automatically target the laser on the samples deposited on the MALDI plate.

Example 2

Matrix/Sample Spot Size and Placement

As discussed above, the impulse-driven momentum transfer depositor is capable of depositing droplets of both small and large volumes. For a peptide separation on a 150 μm ID capillary column, the typical flow rate is 1 μL/min. In this example, the matrix solution is infused post-column at 1 μL/min, or 1:1 with the HPLC. At these flow rates, droplet depositions are typically made every 5 to 60 s. At a total flow rate of 2 μL/min, the volume of the deposited droplets ranges between 160 mL to 2 μL. On an unmodified plate surface, a 2 μL droplet typically dries to approximately 2 mm in diameter. Since in this example the matrix is infused post-column, matrix spots crystallize on the target once the carrier solvents evaporate. Droplets of smaller volume in the droplet range between 160 mL to 2 μL are advantageous in this case, since the droplets will evaporate more quickly, leading to smaller overall sample spots. Generating smaller spots tends to produce fewer "hot spots" of signal intensity during MS analysis, thus facilitating the automation of data acquisition. We note that different matrices can be used to alleviate the occurrence of hot-spots, most notably with α-cyano-4-hydroxycinnaminic acid (CHCA). While the use of CHCA can produce good results, this particular matrix should be used carefully, as it exhibits low solubility in aqueous conditions. In addition, CHCA is a "hot" matrix, which can preclude its use in certain MALDI experiments, such as in the analysis of phosphopeptides, due to in-source fragmentation and metastable ion formation.

As it was pointed out earlier, in interfacing LC to MALDI using off-line fraction collection, the chromatographic separation can be represented by a continuous stream deposited on the collection plate or as discrete spots. A continuous stream would ideally provide superior chromatographic resolution, although in practice, migration of sample components along the continuous stream may broaden chromatographic peaks. Collecting the eluent as discrete spots at a sufficient frequency can preserve the chromatographic integrity of the separation, and serve to concentrate minor components to small areas for improved detection. Thus, producing smaller fractions at greater frequency better preserves the chromatographic separation of components. Larger fractions produced at lower frequency sacrifices separation resolution in favor of greater sensitivity, providing that ion suppression is not severe in both cases. As it is illustrated below, each of these scenarios presents unique advantages, and must be chosen to reflect the needs of the experiment.

Analytical Performance

In evaluating the impulse depositor, it is important to establish that the technology does not hinder the MS sensitivity, nor greatly diminish the LC separation power. To this end, standard samples of GFP and BSA digests were used to benchmark the sensitivity and performance of the technique as a proteomic analysis tool.

Figure 12A:
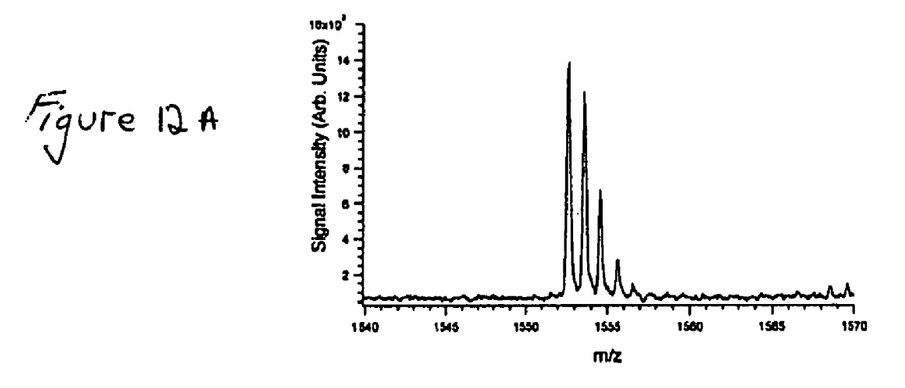
FIG. 12A is a Mass spectrum of 5 fmol pyro-GFP generated by LC-MALDI MS.
Figure 12B:
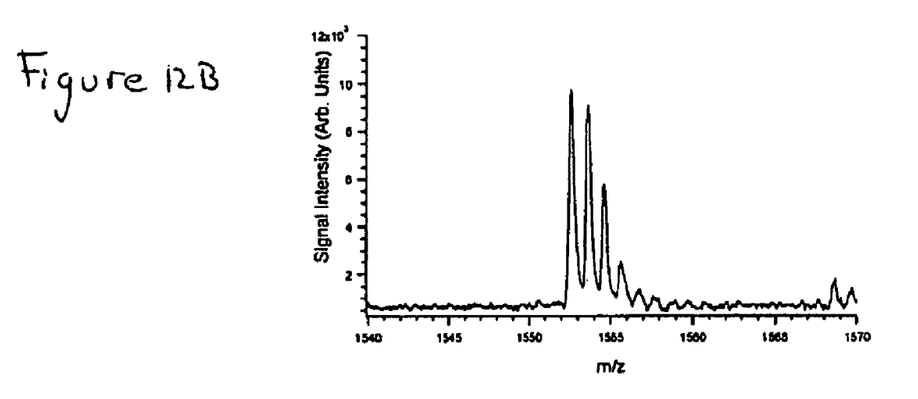
FIG. 12B is a Mass spectrum of 5 fmol pyro-GFP generated direct MALDI-TOF MS.

5 fmol of pyro-GFP was injected into the HPLC for reversed-phase separation, and the corresponding chromatographic peak (approximately 50 seconds wide at the peak base) was collected in one fraction. DHB in methanol was infused post-column, 1:1 with the LC flow rate. The resulting spot was analyzed by MALDI-TOF MS and the result is shown in FIG. 12A. For comparison, a manually spotted sample of the same amount was analyzed using the same instrument and the resulting spectrum is shown in FIG. 12B. As FIGS. 12A and 12B show, the intensity and quality of the mass spectrum for the spot produced by the impulse depositor is comparable to that obtained from a spot prepared manually. This indicates that sample loss is not an issue, and that the matrix crystallization process is not adversely affected by the deposition process.

The ability of the impulse-driven depositor to act as an LC-MALDI interface was demonstrated by fractionating tryptic digests of BSA. Different amounts of a BSA digest were analyzed to gauge the sequence coverage and detection sensitivity. The results are shown in FIGS. 13 and 14. In all cases, chromatographic base-peak widths for peptides from the reversed-phase separation were approximately 40 seconds. For the best sensitivity of detection, fractions of the separation were collected every 60 seconds to reduce the incidence of peak splitting between fractions. Each separation was collected over the entire course of the 50 minutes gradient in one minute fractions, giving 50 discrete fractions. The fractions were each analyzed by MALDI MS/MS. The analysis was automated using the MALDI spot raster and data-dependent subroutines supplied with the instrument. This was done to both reduce the level of user intervention, and to better reflect the current state-of-the art for MALDI MS/MS using the QqTOF instrument.

Figure 13A:
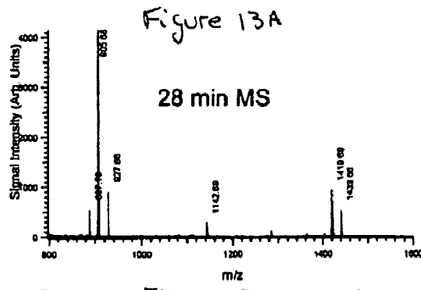
FIG. 13A-13F are LC-MALDI mass spectra of A) fraction 28 and B) fraction 29 of a 200-fmol BSA digest; C) and E) LC-MALDI MS/MS spectra of L421-R433 5 fmol and 200 fmol respectively and D) and F) R360-R371 from 5 fmol and 200 fmol BSA digest.
Figure 13B:
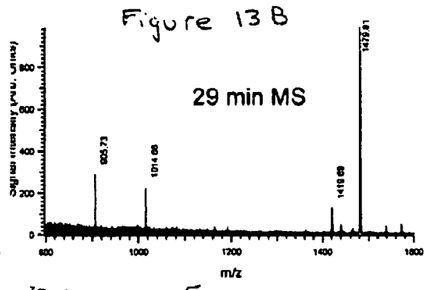
Figure 13C:
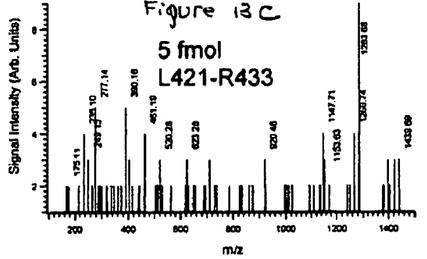
Figure 13D:
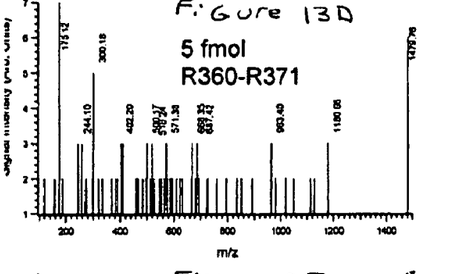
Figure 13E:
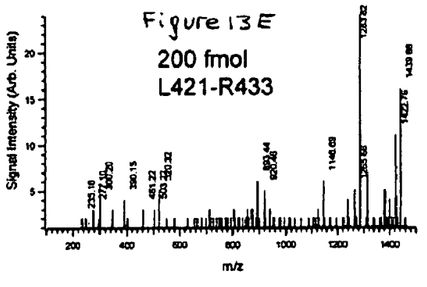
Figure 13F:
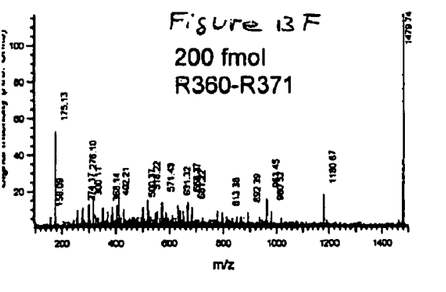
Figure 15A:
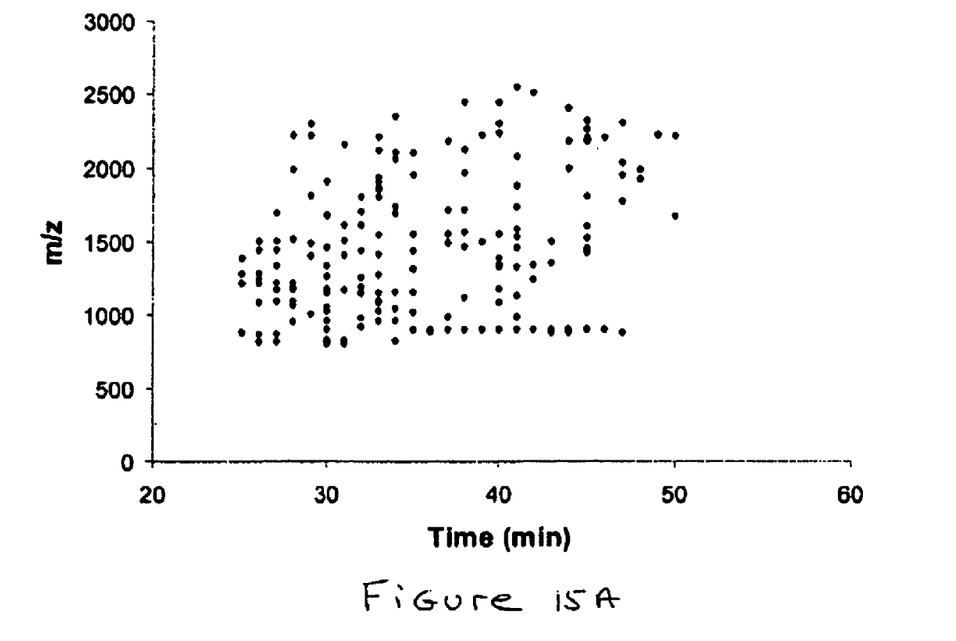
FIG. 15A is a LC-MALDI mass analysis of an *E. coli* protein extract digest in which 25 fractions collected at 60 second intervals result in the detection of 145 unique peptides.
Figure 15B:
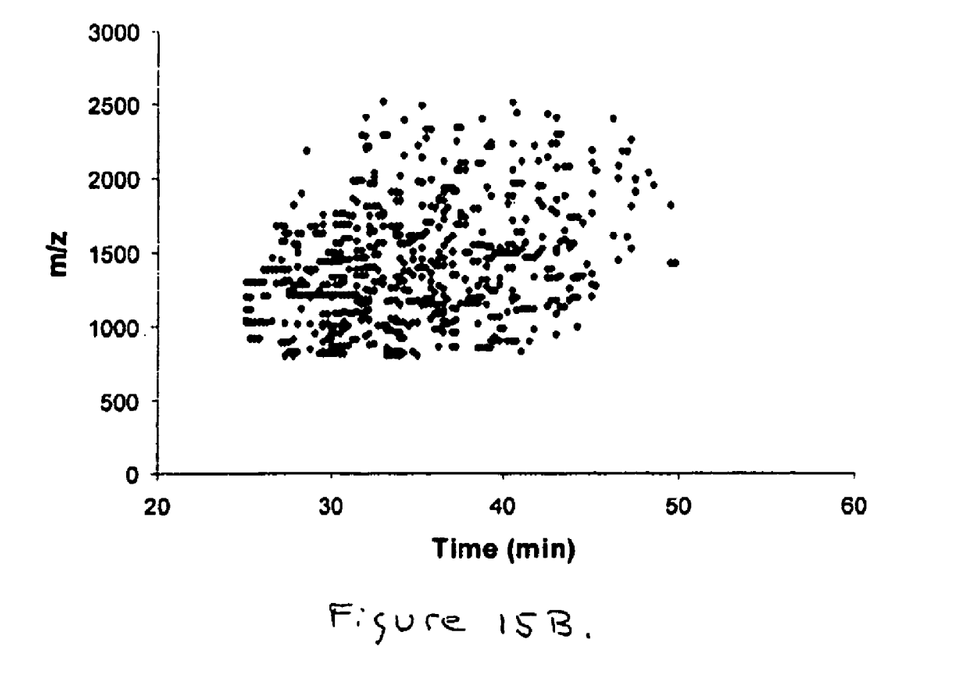
FIG. 15B is a LC-MALDI mass analysis of an *E. Coli* protein extract digest in which 100 fractions collected at 15 second intervals result in the detection of 409 unique peptides.

FIGS. 13A and 13B show MS spectra obtained from two adjacent, representative fractions, 28 min and 29 min, in an LC-MALDI experiment using 200 fmol of the BSA digest. Fractions 28 min and 29 min are representative of the fractions collected for this BSA digest separation, showing only a handful of unique masses in each fraction. The masses identified in each fraction were subjected to MS/MS analysis. FIGS. 13(C-F) show MS/MS spectra from two different BSA digest sample loading amounts, 5 and 200 fmol. Two peptides, L421-R433 and R360-R371, are represented in both samples. The spectra illustrate that even in the 5 fmol sample, the MS/MS data contain enough product fragment ions to identify the peptide using a database search.

The BSA tryptic digest was fractionated and deposited at several sample loading amounts, between 5 fmol and 1 pmol. The resultant MS/MS data were searched using the MASCOT algorithm on the Swissprot database. Characteristic peptides of BSA were identified at all sample loading amounts, and sequence maps were produced to illustrate the change in sequence coverage relative to peptide concentration (FIG.

14). Using the smallest sample amount, 5 fmol, 6% of the sequence is accounted for, with 3 characteristic peptides identified. Thus, the LC-MALDI MS/MS technique using the impulse depositor appears to be applicable to analyze proteome samples containing low fmol of proteins. As expected, to increase sequence coverage, a larger amount of sample is required. Using 1 pmol of BSA digest, sequence coverage of 57% can be achieved, as shown in FIG. 6.

FIG. 14 also illustrates that the collection time for each fraction is sufficient for samples of this complexity. Two experiments were performed at the 200 fmol level: BSA digest was fractionated using 30 s intervals, and again at 60 s intervals. The sequence coverage is approximately equal between the two, indicating that, for this simple protein digest, the analyses of the fractionated peptides are not significantly affected by signal suppression and the spectral recording duty cycle of the mass spectrometer.

The solenoid assembly is mounted on a x,y,z micro-adjustment stage 33—see FIG. 1—(1.75" three axis centre drive positioning stage, Edmund Optics, Barrington, N.J.). The assembly is positioned above motorized translation tables, as shown in FIG. 1B (MX80S, Parker Hannifin, Rohnert Park, Calif.). The motor drivers, computer control card, breakout board and cables required for the motion tables were acquired from the manufacturer. The solenoid is operated by a home-built power supply with an internal function generator which produces a square wave. The power supply can be remotely toggled via a gated logic signal, which is triggered through the break-out board. The motion tables and solenoid power supply are controlled by a program that was written using the supplied software development tools (ACR-View, Parker Hannifin Compumotor Division, Rohnert Park, Calif.).

This *E. coli* protein digest example, along with the analysis of a simple BSA digest, demonstrates that the optimal interval of time for LC-MALDI fractions is dependent on the complexity of the sample. The LC separation efficiency can also play an important role. With the reduction of peptide sample complexity using multidimensional separation, the selection of fractionation interval time can become less important.

While the applicant's teachings are described in conjunction with various embodiments, it is not intended that the applicant's teachings be limited to such embodiments. On the contrary, the applicant's teachings encompass various alternatives, modifications, and equivalents, as will be appreciated by those of skill in the art.

The invention claimed is:

1. An apparatus for generating a fraction from a liquid sample, the apparatus comprising:
    (a) a capillary tube including a capillary tip, the capillary tube mounted within a support tube;
    (b) a moveable element which comprises the capillary tube and the support tube and which further comprises a stop member and a solenoid core, wherein the stop member and the solenoid core each are mounted to the support tube such that the moveable element moves as a unit along a line defined by the support tube and such that the support tube passes entirely through the stop member and the solenoid core;
    (c) an actuating means for displacing the moveable element and connected thereto, the actuating means comprising a solenoid which activates the solenoid core; and
    wherein the stop member is located to limit the travel of the moveable element, whereby, in use, actuation of the actuation means displaces the moveable element from a first position to a second position, wherein in reaching the second position the moveable element is made to abuts the stop member, which rapidly decelerates the moveable element and the capillary tube, to promote the separation of a droplet from the tip of the capillary tube.

2. An apparatus as claimed in claim 1, wherein the actuation means further comprises a spring means, acting on the moveable element, to displace the moveable element to the first position after it reaches the second position.

3. An apparatus as claimed in claim 1, wherein the stop member is generally cylindrical, and wherein a fixed abutment member is located adjacent the stop member and includes an aperture for passage of the support tube and the capillary tube.

4. An apparatus as claimed in claim 1, including means for supporting a support plate for receiving droplets adjacent the capillary tip.

5. An apparatus as claimed in claim 4, including means for locating the support plate at a first position sufficiently spaced from the capillary tip to promote complete separation of larger droplets from the capillary tip before the droplets contact the plate, and a second position in which the plate is located closer to the capillary tube, for enabling smaller droplets to be drawn onto the plate by wicking action for complete separation of the droplets from the capillary tip.

6. An apparatus as claimed in claim 1, the apparatus including a support member and a plurality of capillary tubes, each including a respective capillary tip mounted in the support member, the tips of the capillary tubes being mounted in a generally common plane, for enabling simultaneously deposition of a plurality of fractions onto a plate.

7. An apparatus as claimed in claim 1 wherein the capillary tip is coated with a hydrophobic coating.

* * * * *